(12) United States Patent
Lamberg

(10) Patent No.: US 7,730,891 B2
(45) Date of Patent: Jun. 8, 2010

(54) INTRAORAL MANDIBULAR ADVANCEMENT DEVICE FOR TREATMENT OF SLEEP DISORDERS

(76) Inventor: Steven B. Lamberg, 140 Main St., Northport, NY (US) 11768

(*) Notice: Subject to any disclaimer, the term of this patent is extended or adjusted under 35 U.S.C. 154(b) by 5 days.

(21) Appl. No.: 11/965,161

(22) Filed: Dec. 27, 2007

(65) Prior Publication Data

US 2008/0099029 A1 May 1, 2008

Related U.S. Application Data

(63) Continuation-in-part of application No. 11/416,991, filed on May 3, 2006, now abandoned.

(60) Provisional application No. 60/724,597, filed on Oct. 7, 2005.

(51) Int. Cl.
*A61F 5/56* (2006.01)
*A61C 3/00* (2006.01)

(52) U.S. Cl. .......................................... 128/848; 433/6

(58) Field of Classification Search ................. 128/848, 128/859–862; 433/6; 602/902
See application file for complete search history.

(56) References Cited

U.S. PATENT DOCUMENTS

| | | | |
|---|---|---|---|
| 4,299,568 A * | 11/1981 | Crowley | 433/6 |
| 4,366,815 A | 1/1983 | Broomes | |
| 4,669,459 A | 6/1987 | Spiewak et al. | |
| 4,773,853 A | 9/1988 | Kussick | |
| 4,817,636 A | 4/1989 | Woods | |
| 5,003,994 A | 4/1991 | Cook | |
| 5,085,584 A | 2/1992 | Boyd | |
| 5,177,816 A | 1/1993 | Schmidt et al. | |
| 5,277,202 A | 1/1994 | Hays | |
| 5,313,960 A | 5/1994 | Tomasi | |
| 5,316,020 A | 5/1994 | Truffer | |
| 5,357,981 A | 10/1994 | Eilam et al. | |
| 5,427,117 A | 6/1995 | Thornton | |
| 5,499,633 A | 3/1996 | Fenton | |
| 5,642,738 A | 7/1997 | Lilly, Jr. | |
| 5,795,150 A | 8/1998 | Boyd | |
| 5,915,385 A | 6/1999 | Hakimi | |
| 5,988,170 A | 11/1999 | Thomas | |
| 6,055,986 A | 5/2000 | Meade | |
| 6,092,523 A | 7/2000 | Belfer | |
| 6,129,084 A | 10/2000 | Bergersen | |
| 6,170,485 B1 | 1/2001 | Orrico | |
| 6,231,337 B1 | 5/2001 | Boyd | |
| 6,263,877 B1 | 7/2001 | Gall | |
| 6,386,201 B1 | 5/2002 | Fard | |
| 6,408,851 B1 | 6/2002 | Karell | |
| 6,467,485 B1 | 10/2002 | Schmidt | |

(Continued)

*Primary Examiner*—Patricia M Bianco
*Assistant Examiner*—Tarla R Patel
(74) *Attorney, Agent, or Firm*—Dorr, Carson & Birney, P.C.

(57) ABSTRACT

An intraoral mandibular advancement device to treat sleep disorders in a user having an obstructed airway includes a maxillary appliance with a main body for removable attachment to the maxillary teeth; a protrusive element distending from the central portion of the main body; and retention means extending from the main body for retention of the device on the maxillary teeth during sleep. A mandibular appliance removably attaches to the mandibular anterior teeth and includes a lingual spacer that extends posteriorly from the mandibular anterior teeth. The anterior aspect of the protrusive element of the maxillary appliance contacts the posterior edge of the lingual space and thereby causes mandibular advancement.

14 Claims, 9 Drawing Sheets

U.S. PATENT DOCUMENTS

| | | |
|---|---|---|
| 6,494,209 B2 | 12/2002 | Kulick |
| 6,516,805 B1 * | 2/2003 | Thornton .................... 128/848 |
| 6,526,982 B1 | 3/2003 | Strong |
| 6,548,518 B2 | 4/2003 | Rubin et al. |
| 6,604,528 B1 | 8/2003 | Duncan |
| 6,666,212 B2 | 12/2003 | Boyd, Sr. |
| 6,668,834 B1 | 12/2003 | Zikria |
| 6,675,804 B1 | 1/2004 | Pivovarov |
| 6,729,335 B1 | 5/2004 | Halstrom |
| 6,845,774 B2 | 1/2005 | Gaskell |
| 6,886,566 B2 | 5/2005 | Eubank |
| 6,895,970 B1 | 5/2005 | Lawrence et al. |
| 6,974,837 B2 | 12/2005 | Jerussi et al. |
| 6,979,750 B1 | 12/2005 | Scanlan et al. |
| 7,004,172 B1 | 2/2006 | Zacco |
| 7,174,895 B2 * | 2/2007 | Thornton et al. ............ 128/848 |
| 7,234,467 B2 * | 6/2007 | Ball ........................... 128/848 |
| 2003/0116164 A1 | 6/2003 | Boyd, Sr. |
| 2005/0022824 A1 | 2/2005 | Ball |
| 2005/0288624 A1 | 12/2005 | Boyd |

* cited by examiner

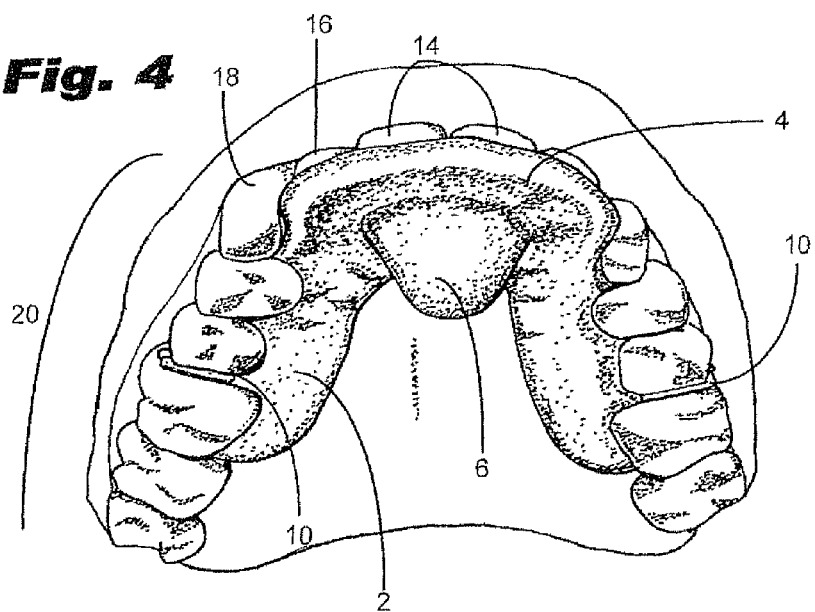
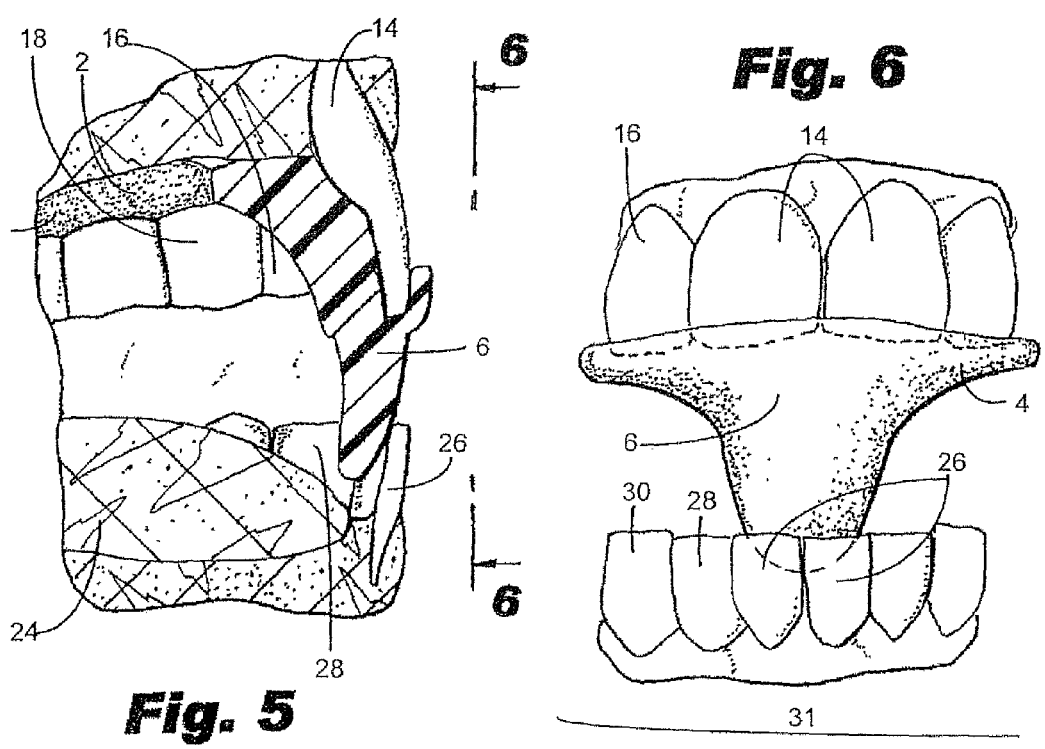

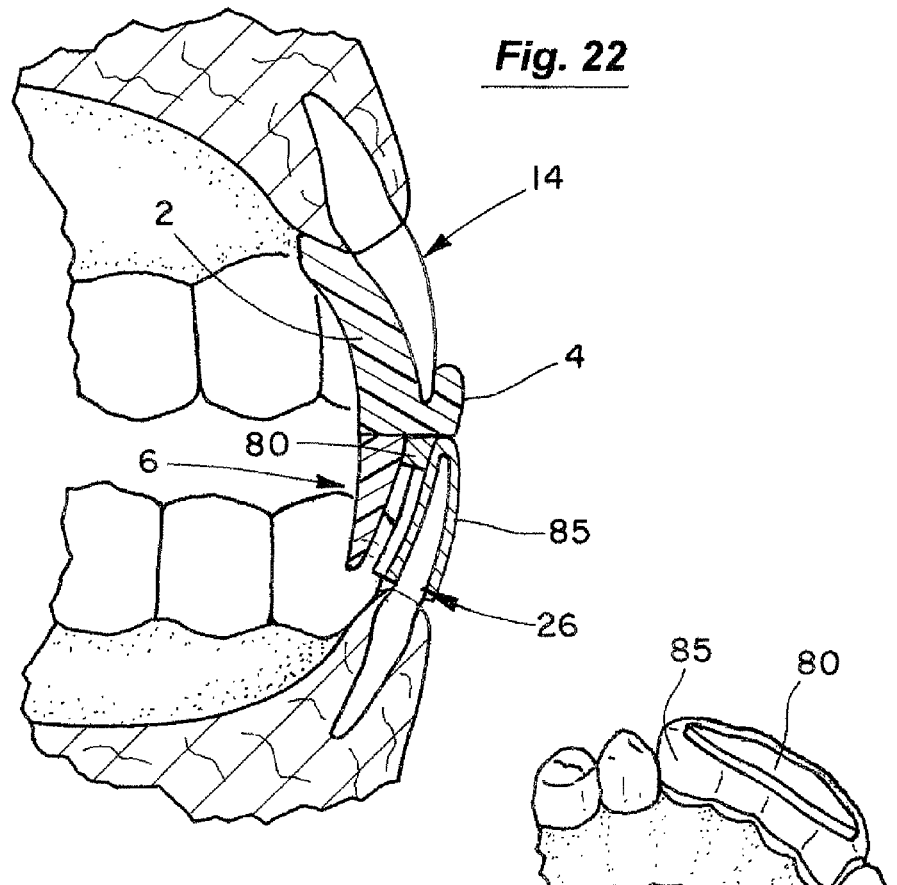
Fig. 22
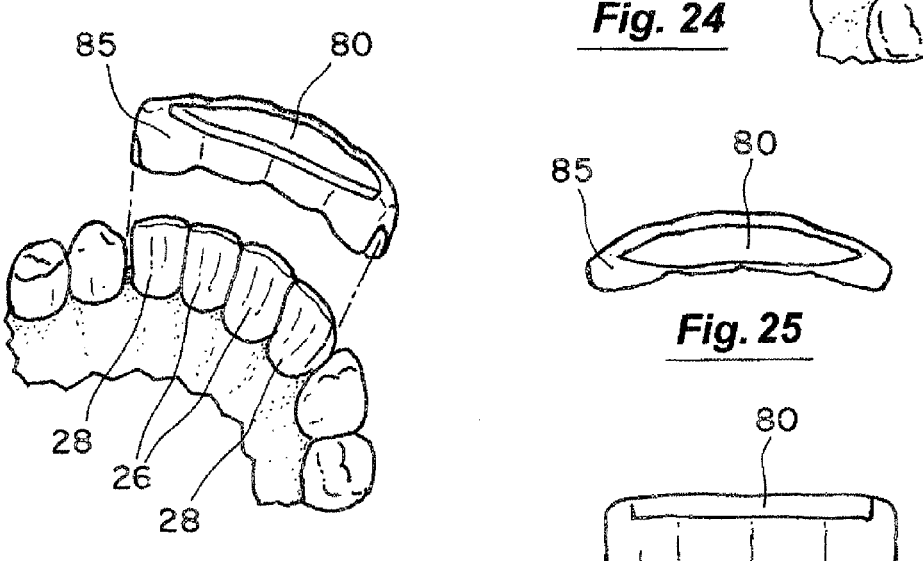
Fig. 24
Fig. 23
Fig. 25
Fig. 26

INTRAORAL MANDIBULAR ADVANCEMENT DEVICE FOR TREATMENT OF SLEEP DISORDERS

RELATED APPLICATIONS

This application is a continuation-in-part of the Applicant's U.S. patent application Ser. No. 11/416,991, filed on May 3, 2006, which claims priority to U.S. Provisional Patent Application Ser. No. 60/724,597, filed on Oct. 7, 2005.

BACKGROUND OF THE INVENTION

1. Field of the Invention

The present invention relates generally to devices for treatment of sleep disorders, and more particularly to an intraoral mandibular advancement device for the treatment of snoring, obstructive sleep apnea, gastroesophageal reflux disease, and bruxism and method for delivering the same.

2. Discussion of the Background

Among the health problems associated with sleep disorders are inter alia, snoring, gastroesophageal reflux disease ("GERD"), obstructive sleep apnea ("OSA"), bruxism, diabetes, high blood pressure (hypertension), and increased risk of stroke or heart attack.

The most widespread sleep disorder is snoring which is a common affliction that affects tens of millions of people worldwide, and can potentially have very serious health and social consequences. Snoring is a sound produced by the vibration of tissue caused by a breathing obstruction during sleep. There are many factors associated with snoring including, but not limited to: heredity, body weight, age, gender, smoking history, nasal, tonsil, or soft palate deformities, use of alcohol, allergies, and sleep position. Commonly, both the snorer and the snorer's sleep partner lose sleep due to the snorer's snoring. The sleep partner is awakened by the sounds caused by snoring, perhaps repeatedly each night. Movement by the sleep partner in subsequently attempting to fall back asleep may then awaken the snorer, if the noise of his or her own snoring has not already done so. Lack of sleep subsequently leads to daytime fatigue, a compromised immune system, poor mental and emotional health, irritability and lack of productivity, which can lead to further repercussions. Snoring is thus problematic for many people.

Obstructive sleep apnea is a potentially lethal sleep and breathing disorder defined as the cessation of breathing for 10 seconds or more (an apnea) at least five times per hour of sleep. In severe cases, individuals can wake up 300 times per night. When breathing is interrupted by an obstruction in the airway, the body reacts by waking enough to start breathing again. Arousals may occur hundreds of times each night, and may not fully awaken the individual, who remains otherwise unaware of the loud snoring, choking and gasping for air typically associated with OSA.

Although not all snorers have OSA, snoring is a cardinal symptom of OSA and clearly indicative of and associated therewith. Many OSA sufferers do not receive a sufficient amount of sleep due to repeated apneatic events and arousals which act to prevent REM and deep stage sleep, which can lead to chronic daytime exhaustion and long-term cardiovascular stress. OSA is the direct cause of at least 38,000 deaths each year. An estimated 30 million Americans suffer from some degree of OSA, yet less than 3% are currently undergoing any type of treatment.

Pathogenesis of OSA involves a combination of reduced upper airway size and altered upper airway muscle activity, which causes oral tissue to collapse, and hence a blockage to occur. Other factors which are thought to contribute to OSA include tongue size, soft palate volume, a retrognathic mandible, an anteroposterior discrepancy between the maxilla and the mandible, and obesity.

Snoring and OSA are often associated, as generally both are caused by blockage of the pharyngeal airway by, for example, excess tissue when various muscles of the body, including the tongue, relax. As the tongue relaxes, it moves posteriorly, blocking the breathing airway. When the breathing airway is blocked, exhaled air is forced through the airway with increased velocity thereby causing vibration of the tongue, tissue, or other obstruction, thereby creating noise. Snoring is caused by the partial obstruction of breathing during sleep while OSA occurs when the tongue and soft palate collapse onto the back of the throat and completely block the pharyngeal airway, thereby stopping breathing during sleep and restricting the flow of essential oxygen. Thus, a correlation between snoring and OSA is generally recognized in the medical community.

Many attempts have been made to reduce or eliminate snoring and OSA in individuals. Various types of surgery, including tracheostomy, surgery of the soft palate and oropharynx, and reconstructive surgery have been utilized in the treatment of snoring and OSA. Invasive surgery however is costly and not without risk, which effectively eliminates this modality as a truly viable solution to snoring and OSA for the general population. Indeed, many practitioners and patients alike would generally seek to avoid surgical intervention and would welcome a minimally invasive route—a general object and feature of the instant invention.

It has been recognized that opening or enlarging an airway that may be constricted due to collapse of tissue about the oropharynx will normalize the airflow to the lungs and in doing so will have a direct effect of resolving snoring and OSA as well as diminishing pressure fluctuations in the esophagus which have been associated with GERD. Known in the art are devices (heretofore cumbersome or ineffective) which are designed to restrict the velocity of the ingress and egress of air with the goal of reducing or eliminating snoring. It is scientifically concluded herein that by opening the aperture of the airway and maintaining the same, the consequences of a collapsed airway are avoided. When the airway is collapsed, the velocity of air flow increases and causes the vibration of the tongue, soft palate, and other tissue present in the pharyngeal wall during sleep. Thus, when expanded and maintained by the invention herein, the airflow is also maintained and snoring and OSA (where it theretofore resulted therefrom) are minimized or eliminated.

For example, U.S. Pat. No. 6,263,877 to Gall shows a device which essentially consists of a mouth guard with a small aperture for which are can pass through. The amount of air flow is therefore directly proportional to the size of the aperture. U.S. Pat. No. 5,642,738 to Lilly, Jr. shows a device which is designed to eliminate snoring via a membrane which is placed on the exterior surface of the anterior teeth to reduce the volume of air which is allowed to flow in and out of the mouth. U.S. Pat. No. 4,817,636 to Woods likewise shows a device which seeks to eliminate snoring via a membrane which is placed on the exterior surface of the anterior teeth to reduce the volume of air which is allowed to flow in and out of the mouth. Yet, reduction of airflow can cause a cascade of other symptomology and situations, including potential OSA.

Also known in the art are devices which seek to reduce or eliminate snoring or OSA by inhibiting vibration of the soft palate. For example, U.S. Pat. No. 6,467,485 to Schmidt shows a device made of a flexible material which is placed over the soft palate in an attempt to inhibit vibration of the soft palate. U.S. Pat. No. 4,669,459 to Spiewak shows an intraoral device which seeks to eliminate snoring by positioning a button on the soft palate to prevent vibration thereof. Yet, such devices do not address the source of the problem or intervene to increase the airway (as does the instant invention), and thus the cascade effect is still a present risk if such devices are employed.

Various devices have sought to alleviate snoring by aiming to keep the pharyngeal airway open to prevent the collapse of the tongue and soft tissues in the back of the throat, yet are bulky and uncomfortable, often resulting in reduced patient compliance. For example, U.S. Pat. No. 6,386,201 to Fard shows a pillow which seeks to keep the user's head in proper position to make snoring less likely. U.S. Pat. No. 4,366,815 to Broomes and U.S. Pat. No. 5,357,981 encompass other designs aimed at maintaining the user's body in a position which makes snoring less likely. U.S. Pat. No. 6,668,834 shows a device which seeks to eliminate or reduce snoring by maintaining the user's chin above the user's chest while in the supine position in order to facilitate breathing as well as to aid in the prevention of snoring.

Positioning of the body does not eliminate the cause of snoring. Since tongue posture appears to have a substantial effect on upper airway morphology, several devices show a design which seeks to hold the tongue in a forward position in order to increase the diameter of the pharyngeal airway during sleep. For example, U.S. Pat. No. 6,494,209 to Kulick shows a device which consists essentially of a mouthpiece with an anterior suction mechanism which creates a vacuum which acts to maintain the tongue in an anterior position. U.S. Pat. No. 6,408,851 shows a device which clamps the tongue in order to maintain the tongue in a forward position. U.S. Pat. No. 6,055,986 to Meade shows a device for the reduction of snoring which encompasses both upper and lower positions which together form a cavity which encompasses the user's tongue when in use to maintain the tongue in a predetermined position or to prevent the tongue from moving posteriorly and thus blocking the pharyngeal airway. U.S. Pat. No. 5,988,170 shows a snoring prevention apparatus consisting essentially of a mask having a tongue depressing member, which acts to maintain the tongue in an anterior position during use. U.S. Pat. No. 6,845,774 to Gaskell shows a mandibular splint which acts to maintain the user's jaws at a predetermined space apart to prevent the tongue from moving posteriorly in order to open the breathing passage. One can only image how truly uncomfortable such devices must be if used at all, and thus the likelihood of patient compliance is small to nil.

There is also recognition of those of ordinary skill in the art of a correlation between OSA and nocturnal gastroesophageal reflex disease ("GERD"). Both OSA and GERD involve a reduction in air pressure in the trachea and esophagus caused by blockage during sleeping, thereby resulting in an increase in the draw of pressure through the esophagus as the diaphragm distends. While the body tends to increase breathing by such distention, the blockage results in the pulling of fluid upwardly in the esophagus and hence results in GERD for the snorer or OSA patient. Yet, the currently recommended solutions involve some version of a "CPAP" (continuous positive airway pressure) or pharmacological intervention. The former involves a face mask and a pump to provide pressure directly to the trachea of the patient which is cumbersome and unaesthetic. The latter obviously includes a plethora of side effects associated with the pharmacology employed, while not directly addressing the physical/mechanical source of the problem.

It is herein recognized that advancing the mandible in an anterior position relative to the maxilla during sleep opens the pharyngeal airway by indirectly urging the tongue forward to stimulate activity of the muscles in the tongue and thereby also increases the forward rigidity of the tongue. Since the tongue attaches to the posterior portion of the mandibular symphysis, advancing the mandible forward relative to the maxilla also pulls the tongue forward, thus preventing the tongue from obstructing the pharyngeal airway. Since the palatoglossus muscle attaches from the tongue to the soft palate, resultant forward movement of the tongue thereby creates tension on the soft palate thereby reducing vibration. Mandibular advancement devices therefore function to move the lower jaw, and hence the tongue forward to open the oropharynx. Snoring thus decreases proportionally with the increase in airway size or diameter.

It should therefore be appreciated that by so urging, and as an object of the instant invention, there can be a positive effect on reduction of snoring and OSA, and also upon GERD which is associated with the existence of large intrapleural pressure swings, which occur during apneatic events.

A number of different appliances for the treatment of snoring or OSA which move the mandible forward relative to the maxilla have been suggested, yet such devices typically fit over both the arches of teeth and are thus large and cumbersome. Several such different devices allegedly for the treatment of snoring or OSA move the mandible forward relative to the maxilla can be observed in the following U.S. patents: Halstrom, U.S. Pat. No. 6,729,335; Thornton, U.S. Pat. No. 6,516,805; Orrico, U.S. Pat. No. 6,170,485; Belfer, U.S. Pat. No. 6,092,523; Bergersen, U.S. Pat. No. 6,129,084; Fenton, U.S. Pat. No. 5,499,633; Tomasi, U.S. Pat. No. 5,313,960; Hays, U.S. Pat. No. 5,277,202; Shapiro, U.S. Pat. No. 5,177,816; and Strong, U.S. Pat. No. 6,526,982. These devices consist essentially of acrylic or elastomeric upper and lower bite trays which fit over both the maxillary and mandibular teeth, respectively, with some connecting means to shift the user's bite so that the mandible is urged forward relative to the maxilla. Thus, to achieve anterior movement of the mandible, these devices essentially move one jaw against the other in a cumbersome manner which no doubt has an effect on patient compliance.

Such appliances which fit over both arches of teeth were derived from the orthodontic domain which it has ordinarily been considered prudent to cover all the teeth in order to prevent undesired movement (eruption) of any teeth not covered by the device resulting from a lack of opposition. Studies have shown however that partial coverage of the teeth during sleep does not result in undesired eruption of uncovered teeth, therefore rendering previous concerns unwarranted. These devices are therefore unnecessarily bulky and difficult to fit over the user's teeth. Bulky devices also occupy a large portion of the oropharyngeal volume, thus making breathing, and the passage of air around the bulky device difficult—the very antithesis of the goal herein sought: to increase the dimensional size of the airway. Breathing difficulty substantially reduces the efficacy of such devices to treat snoring or OSA, let alone the secondary effects of GERD caused by airway obstruction.

Many devices claimed for treatment of snoring or OSA which move the mandible forward relative to the maxilla fit over both the arches of teeth and also move one jaw substantially against the other, thereby posing other potentially damaging effects. Mandibular advancement devices that fit over both the maxillary and mandibular teeth are typically held nearly stationary, thereby restricting movement, causing discomfort, and potential permanent repositioning of the jaw.

Since these types of devices restrict the user's natural lateral movements as well as anterior and posterior movements, continued use can potentially aggravate the tempromandibular joint (TMJ) and the related facial musculature, which would worsen over time, with continued use. Thus, it is an object of the instant invention to permit such movements, increase comfort and compliance, and additionally avoid TMJ effects.

Also shown in the art are appliances which are worn only upon the user's maxillary teeth, thus leaving the mandibular teeth uncovered. For example, U.S. Pat. No. 5,915,385 to Hakimi discloses a snore and stress relief device which seeks to engage the user's upper dentition and includes an anterior extension which appears to advance the user's lower jaw forward with respect to the user's upper jaw such that the user's upper airway is enlarged and the passage of air through the upper airway is facilitated. The device disclosed in Hakimi has a posterior position which fits against the dorsal surface of the user's soft palate to secure the device, which may also cause gagging or other discomfort, thus reducing or eliminating efficacy.

Although prior devices may have effect in treating snoring and OSA by moving the mandible forward relative to the maxilla to open the airway, such devices have unwanted side effects or are ineffective due to, inter alia, their bulk. As stated herein, many of the devices which appear to be designed to alleviate snoring and OSA restrict the user's natural nocturnal movements of the lower jaw which can potentially aggravate the tempromandibular joint and related jaw muscles and ligaments. Due to their bulk, devices prior to that shown herein that claim a design to eliminate or reduce snoring or OSA rely largely on the user's ability to breath through the nose. Thus, such devices would not function properly with users who have difficulty breathing through their noses. Furthermore, many of these devices must be removed or unhinged or otherwise disengaged to allow the user freedom to speak, swallow, or drink water, thus creating serious inconvenience to the user (and poor aesthetics). It is thus an object of the instant invention to overcome these shortcomings in prior devices.

Gastroesophageal reflex disease ("GERD"), also known as acid reflux, is a chronic condition which affects at lest 5 to 7% of the global population, including over seven (7) million people (reportedly as high as 30 million) in the United States alone. GERD is characterized by movement of the liquid contents of the stomach from the stomach into the esophagus. Almost everyone experiences gastroesophageal reflux at some time or another. When reflux is frequent or severe enough to cause more significant problems, it is characterized as GERD. GERD can cause serious complications including inflammation of the esophagus from stomach acid that causes bleeding or ulcers. Asthma, chronic cough, and pulmonary fibrosis may be aggravated or even caused by GERD.

The liquid content of the stomach typically contains acid, pepsin, and bile, which are harmful to the delicate lining of the esophagus when regurgitated. Damage to the esophageal lining can result in scarring and narrowing of the esophagus, and can be linked to the development of esophageal cancer.

Pressure created by the lower esophageal sphincter ("LES") and diaphragm surrounding the LES ordinarily create a barrier to reflux. During snoring or an apneatic event, however, a large negative intrapleural pressure swing often occurs facilitating reflex events. Thus, blockage of the esophageal airway creates a negative pressure which allows reflux to occur by facilitating the upward movement of the liquid contents of the stomach. When in an upright position, most refluxed liquid naturally flows back into the stomach due to the force of gravity. When in a supine position however, most refluxed liquid is forced upwardly, into the esophagus, typically causing damage thereto. Due to the increased potential for reflex during sleep in the supine position, it is therefore beneficial to have a method of treatment which can be applied during sleeping hours to maintain the pressure system without creating negative esophageal pressure and concomitant potential reflex. See, e.g., Green, B T, et al., *Marked Improvement in Nocturnal Gastroesophageal Reflux in a Large Cohort of Patients with Obstructive Sleep Apnea with Continuous Positive Airway Pressure*, Arch. Intern. Med., 2003 Jan. 13; 163(1):41-5.

Symptoms of gastroesophageal reflux disease include regurgitation, heartburn, difficulty swallowing, chest pain and nausea. As a chronic disease, treatment of gastroesophageal reflux disease typically continues indefinitely. It is therefore preferable that a method of treatment for gastroesophageal reflux disease is comfortable for nightly use.

Among the heretofore shown methods used to treat GERD are the use of antacids, histamine antagonists, proton pump inhibitors, promobility drugs which stimulate the muscles of the gastrointestinal tract, foam barriers which form a physical barrier to the reflux of liquid, and surgery. For example, U.S. Pat. No. 6,979,750 to Scanlan et al. shows thyronamine derivatives and analogs for the treatment of GERD. U.S. Pat. No. 6,974,837 to Jerussi et al. shows pharmaceutical compositions that comprise a racemic or optically pure sibutramine metabolite and a phosphodiesterase inhibitor for the treatment of GERD. U.S. Pat. No. 6,548,518 to Rubin et al. shows the use of norcisapride in combination with proton pump inhibitors or H2 receptor antagonists for the treatment of GERD.

Continuous Positive Airway Pressure ("CPAP") therapy has been shown to reduce GERD by increasing intra-esophageal pressure. Yet these devices have drawbacks, as herein stated, and thus are not of choice especially if non-invasive, easily placeable and removable, and not uncomfortable alternatives, like that of the instant invention, are available. Although there exists a broad range of dentally-retained intraoral appliances worn at night for the treatment of snoring and obstructive sleep apnea, no such appliances heretofore satisfied such criteria and, also, were directed at treatment of GERD. It is thus an object of the instant invention to present a noninvasive alternative to drug therapy and surgical intervention for the treatment of GERD.

Bruxism is the technical description for clenching, gnashing or grinding of teeth. Bruxing is common in almost all individuals and can occur subconsciously or when an individual becomes stresses or aggravated. The risk of bruxism increases with age, stress, and use of caffeine, nicotine and other drugs. In most cases, bruxism is mild and does not require treatment. When bruxing is more frequent however it can lead to jaw disorders, headaches, earaches, damaged teeth, chronic facial pains, and other problems. Therapy such as muscle relaxers and botox are currently used as remedies for bruxism. Alleged dental solutions include mouth guards and splints which appear to be designed to prevent damage to the teeth or decrease muscle activity. For example, U.S. Pat. No. 7,004,172 to Zacco shows a device which seeks to separate a user's mandibular and maxillary teeth by creating a space in the posterior portion of said mandibular and maxillary teeth. U.S. Pat. No. 6,886,566 to Eubank shows a device having a multiplicity of arches which act to maintain the tempromandibular joint in the proper position in an attempt to prevent bruxing. U.S. Pat. No. 6,675,804 to Pivovarov shows a device which maintains the tongue and mandibular and maxillary teeth in a position which seeks to eliminate the potential for bruxism. However, the device in Pivovarov encompasses both the mandibular and maxillary teeth, and is bulky and uncomfortable. U.S. Pat. No. 6,604,528 to Duncan shows a device that contains guide elements to position the device relative to the mouth and teeth and at the same time appears to prevent mating of the teeth when the mouth is closed and therefore gnashing or grinding of teeth during sleep. Yet, such devices heretofore shown in the art that are aimed to prevent bruxism or damage caused by bruxing fail to address or effectively aid in the treatment of snoring, OSA and GERD. An object and feature of the instant invention is the separation of the posterior teeth thereby eliminating the possibility of clenching which is a prerequisite for bruxing, while nonetheless permitting nocturnal jaw movements.

Hence, an object of the instant invention is the presentation of an effective intraoral appliance for treatment of sleep disorders including snoring, OSA, GERD or bruxing by moving the user's mandible forward with respect to the user's maxilla in order to open the airway in a manner which is comfortable, easily placeable, and without adverse effects. As shown above, prior devices have struggled to optimize the size and design parameters to facilitate the dual goals of comfort and effectiveness, but have woefully failed to achieve this goal. Thus, compliance is a predominant issue.

SUMMARY OF THE INVENTION

In accordance with the teachings of the present invention, an intraoral mandibular advancement device is provided which substantially eliminates or reduces disadvantages associated with prior devices in connection with sleep disorders. More specifically, it is a feature of the instant invention to provide an intraoral mandibular advancement device for the treatment of sleep disorders, primarily snoring, and also including OSA, GERD or bruxism by, inter alia, urging the user's lower jaw forward via a protrusive element which pushes against the lingual surfaces of the anterior mandibular teeth, all as more fully shown herein.

In particular, an intraoral mandibular advancement device is shown to treat problems associated with sleep disorders in a user having an obstructed oropharyngeal space, the disorders including, without limitation, snoring, obstructive sleep apnea, gastroesophageal reflex disease or bruxism having a main body for attachment to the user's mouth and having a central portion; a protrusive element distending from the central portion of the main body such that when worn by the user the element causes mandibular advancement sufficient to expand the oropharyngeal space and reduce the obstruction; and a retention element extending from the main body for retention of the device in the user's mouth when worn during the user's sleep state. The main body is either complementary with the user's palate and lingual surfaces of the anterior maxillary teeth, and extends downwardly against the lingual surfaces of the user's anterior mandibular teeth, or can be customized to rest against two, four or six of the user's front teeth.

The protrusive element is distension between 5 and 15 mm, and optimally 10 mm downwardly from the main body, and can be adjusted anteriorly or posteriorly such that the advancement of the protrusive element relative to the main body ranges between 1 and 7 mm. The advancement of the protrusive element relative to the main body commences at a position approximately 3.0 to 4.0 mm or approximately half of the user's maximum protrusive range and is advanced, if required therefrom. A method for diagnosis and prescription of the device is also shown.

More particularly, an intraoral mandibular advancement device is provided which includes a main body comprised of materials providing the requisite strength and flexibility such as polymeric materials, acrylic materials, natural materials, rubbers, metals, silicones, vinyls, elastomeric materials, hard plastic, thermal plastic, and thermosensitive acrylic resin and combinations thereof. The preferred embodiment of the instant invention largely resembles an orthodontic retainer, yet encompasses additional elements in order to urge the user's lower jaw forward relative to the user's upper jaw for the elimination or reduction of sleep disorders including primarily snoring, as well as obstructive sleep apnea, gastroesophageal reflux disease. It is preferable that the lower jaw is advanced beginning at least 3.0-4.0 mm relative to the maximum intercuspal position ("MIP") and moved anteriorly as required to achieve the goals stated herein. This 3.0-4.0 mm shift represents approximately 50% of an individual's maximum active protrusive range. The optimal degree of offset will vary with each user and hence adjustability is provided.

For the purpose of comfort, it is preferable that the lower jaw is not moved further anteriorly than necessary to gain patency in the airway. The instant invention includes a main body which is preferably complementary with a user's palate and lingual surfaces of the maxillary teeth. The main body is thus essential horseshoe-shaped. Custom fitting with the user's dental arch ensures comfort while at the same time acting as a retention mechanism to secure the device in the user's mouth.

Extending from the central portion of the main body of the instant invention is a protrusive element which, while in use, rests behind the lingual surfaces of the user's anterior mandibular teeth in a manner to urge the lower jaw anteriorly. The length of the protrusive element is approximately 10.0 mm, yet the precise length will vary with the structure of the mouth of each user, and is customized to facilitate comfort and efficacy. Anterior movement of the mandible by the instant device serves to urge the attached tongue forward as well as a result of the attachment, thereby achieving all of the aforementioned goals, objects and features. For example, said anterior movement of the mandible and tongue decreases the negative pressure in the esophagus and thereby reduces or eliminates GERD (when the same is caused thereby). Importantly, mandibular advancement, or protrusion, also creates more space behind the tongue and therefore increases the airway diameter in the oropharynx.

Said protrusive element further serves to position the mandible in place to inhibit the tongue from moving posteriorly during sleep in the supine position. When the instant inventive device is inserted in the user's mouth, the protrusive element fits snugly against the lingual surface of a plurality of the anterior mandibular teeth. When in use, the device is fixed between the user's maxillary arch and anterior mandibular teeth thus moving the mandible forward relative to the maxilla. As retention is a critical element in the design of any intraoral appliance, the device of the instant invention is designed to be retained in the user's mouth while withstanding the user's ordinary movements, which may include teeth grinding.

Said protrusive element, like the main body, can be comprised of materials known in the art which provide the requisite strength and flexibility such as polymeric materials, acrylic materials, natural materials, rubbers, metals, silicones, vinyls, elastomeric materials, hard plastic, thermal plastic, and thermosensitive acrylic resin and combinations thereof.

Retention of the device in the user's mouth during use is also achieved via a plurality of clasps which surround the exterior of the user's teeth. Said clasps are arranged at different positions of the device for optimal comfort and effectiveness. In one embodiment of the instant invention, said clasps are posteriorly positioned over the upper left and right molars, on opposite sides of the mouth, and anteriorly positioned from cuspid to cuspid, on opposite sides of the mouth.

Retention of the device may also be achieved by a retention arc formed by the main body in which the anterior maxillary teeth are fitted. The length of the retention arc may vary to encompass a plurality of teeth.

In one embodiment of this instant invention, said protrusive element is adjustable, in order to incrementally advance the degree of displacement between the main body and protrusive element. It is recognized that the smallest amount of mandibular advancement necessary to attain a patent airway should be used to maximize both efficacy and comfort. Yet, even in the non-adjustable version of the instant invention, material may be added or extracted to thereby modify dimensions to afford such maximization.

At least one embodiment of the instant invention can be fitted onto two, four or six anterior maxillary (upper) teeth while leaving mandibular teeth and the posterior maxillary teeth and remaining anterior maxillary teeth, if any, uncovered. Dispersing pressure over multiple teeth eliminates placing undue pressure on the teeth while at the same time eliminating the potential that the teeth will be reoriented.

While in use, the instant invention is positioned on a varying number of anterior maxillary teeth thus preventing the posterior teeth to contact. Said contact on the anterior mandibular teeth, in addition to the lack of contact on the posterior teeth, prevents the elevator muscles from contracting thereby precluding clenching and grinding. Since the jaw muscles are inhibited from contracting, clenching and bruxing (teeth grinding) is made less likely, thus rendering the instant invention effective in the treatment of bruxism. In addition, even if there is an occurrence of clenching or bruxing, the negative impact on the posterior teeth would be alleviated as a result of the inability of the posterior opposing teeth to contact each other.

Mandibular advancement effects the anatomy of the upper airway to allow increased air flow by, inter alia, (a) elevating the base of the tongue in resting position; (b) tensing the palatoglossus muscles and urging the soft palate (uvula) forward; (c) decompressing tissues around the pharynx and allowing the pharynx to expand; (d) stabilizing the lateral pharyngeal wall by applying tension to the pterygomandibular raphe, which is coupled to pharyngeal constrictors; and (e) splaying the tonsillar arches formed by the palatoglossus and the palatopharyngeal muscles, which leads to further stabilization of the lateral pharyngeal wall.

Due to its low bulk, the device of the instant invention is enclosed completely within the oral cavity of the user during use to permit a comfortable fit during use. Since the device fits completely within the oral cavity of the user, the device of the instant invention thereby permits adequate lip seal. Such an intraoral device as that shown herein permits the lips of the user to close thereby enjoying higher patient compliance and is also simpler for the user to adapt to using, thus creating less interference with sleep.

A principal feature and advantage of the instant invention is the provision of a device which is effective in the treatment of sleep disorders, primarily snoring, OSA, GERD or bruxism, as described.

A further feature of the instant invention is the provision of a device which advances a user's mandible relative to the user's maxilla.

A further feature of the instant invention is the provision of a device which minimizes the amount of materials used while advancing a user's mandible relative to the user's maxilla.

A further feature of the instant invention is the provision of a device which advances a user's mandible relative to the user's maxilla customized to fit a user's unique mouth structure.

A further feature of the instant invention is the provision of a device which opens a user's airway and prevents the same from subsequently becoming obstructed by the user's own oral tissue structure.

A further feature of the instant invention is the provision of a device which advances a user's mandible relative to the user's maxilla which is also removably maintained solely upon the user's upper dentition or palate.

A further feature of the instant invention is the provision of a device which advances a user's mandible relative to the user's maxilla which is also of low bulk.

A further feature of the instant invention is the provision of a device which advances a user's mandible relative to the user's maxilla which also allows the user to close his or her mouth so as to allow lip seal.

A further feature of the instant invention is the provision of a device which advances a user's mandible relative to the user's maxilla while also allowing adequate tongue space for comfort and facile movement of the tongue.

A further feature of the instant invention is the provision of a device which prevents posterior movement of the tongue by advancing the user's mandible relative to the user's maxilla to maintain the tongue in the proper position and to permit the unobstructed passage of inspiratory and expiratory air.

A further feature of the instant invention is the provision of a device which can be incrementally adjusted to vary the degree of anterior protrusion for optimal placement behind the user's anterior mandibular teeth.

A further feature of the instant invention is the provision of a device which advances a user's mandible relative to the user's maxilla without influencing occlusion (bite).

A further feature of the instant invention is the provision of a device which provides a comfortable fit for the user.

A further feature of the instant invention is the provision of a device which allows lateral movement of the mandible relative to the maxilla as well as anterior/posterior movement relative to the maxilla, for reasons of comfort.

A further feature of the instant invention is the provision of a device which allows the user freedom to speak, swallow, or drink water without removing, unhinging, or otherwise disengaging the device.

A further feature of the instant invention is the provision of a device which precludes the contacting of posterior teeth by utilization of an anterior area of contact which thereby prevents clenching and bruxing.

The above description sets forth rather broadly the more important features of the present invention in order that the detailed description thereof that follows may be understood, and in order that the present contributions to the art may be better appreciated. Other objects and features of the instant invention will become apparent from the following descriptions considered in conjunction with the accompanying figures. It is to be understood, however, that the drawings are designed solely for the purposes of illustration and not as a definition of the limits of the invention, for which reference should be made to the appended claims.

BRIEF DESCRIPTION OF THE DRAWINGS

In the drawings, wherein similar reference characters denote similar elements throughout the several views:

FIG. 4 is a bottom view of one embodiment of the intraoral mandibular advancement device of the instant invention shown during use;

FIG. 5 is a cross-sectional view of one embodiment of the intraoral mandibular advancement device of the instant invention shown during use, as shown in FIG. 6;

FIG. 6 is a frontal perspective view of one embodiment of the intraoral mandibular advancement device of the instant invention;

FIG. 22 is an enlarged cross-sectional view of the embodiment of the invention corresponding to FIG. 21 in a patient's mouth.

FIG. 23 is a detail exploded perspective view showing the mandibular appliance being placed over a user's mandibular incisors 26, 28.

FIG. 24 is a detail perspective view corresponding to FIG. 23 after the mandibular appliance has been attached to the user's mandibular incisors 26, 28.

FIG. 25 is a top view of the mandibular appliance.

FIG. 26 is a rear elevational view of the mandibular appliance.

DETAILED DESCRIPTION OF THE INVENTION

Figure 1:
FIG. 1 is a perspective, environmental view of one embodiment of the intraoral mandibular advancement device of the instant invention shown during use in phantom.

Shown in FIG. 1 is a perspective, environmental view of one embodiment of the intraoral mandibular advancement device of the instant invention shown worn by a typical person in the supine position. Device 1 permits the user to voluntarily open and close his or her mouth to speak or drink a glass of water, while also allowing for natural movement during sleep. As shown in FIGS. 2-6, intraoral mandibular advancement device 1 has a main body 2 which is customized to fit along the lingual surface of the user's maxillary teeth 20 and hard palate while leaving the soft palate and middle area of the palate uncovered during use. It should be appreciated by one of ordinary skill upon reading the text hereof and the figures herein, that the instant inventive device 1 disallows contact of the posterior teeth against each other thereby preventing contraction of the elevator muscles of the jaw and hence bruxism, as well as opening the airway as explained, thereby eliminating other sleep disorders including snoring, OSA or GERD.

Figure 2:
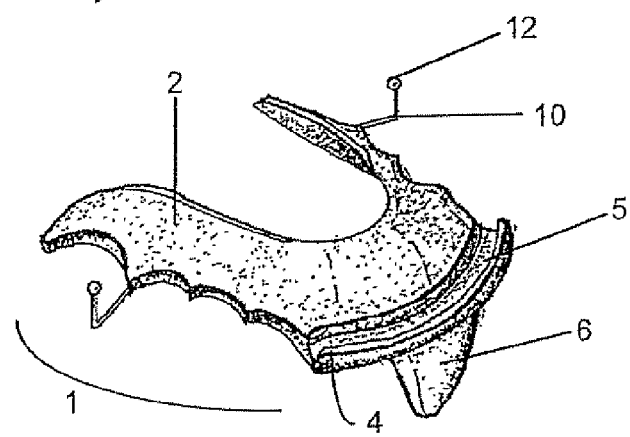
FIG. 2 is a topographic view of one embodiment of the intraoral mandibular advancement device of the instant invention.
Figure 3:
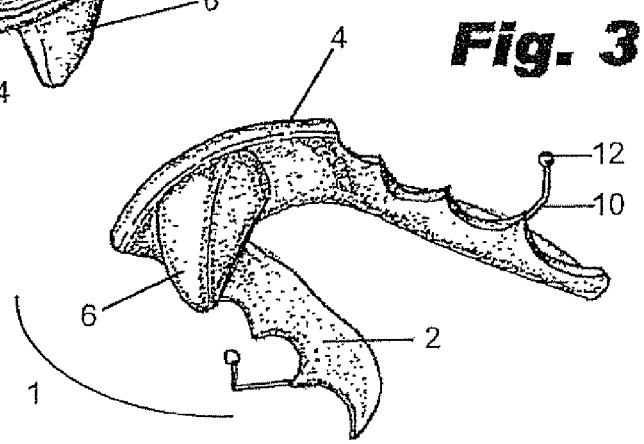
FIG. 3 is a bottom perspective view of one embodiment of the intraoral mandibular advancement device of the instant invention.
Figure 7:
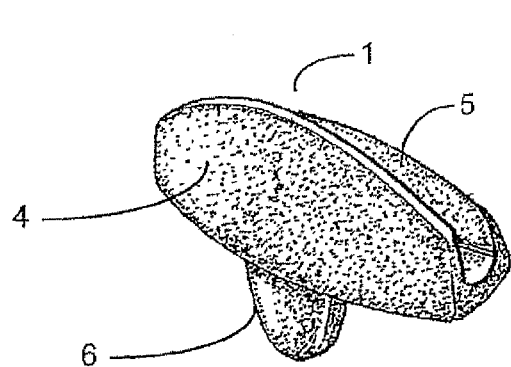
FIG. 7 is a perspective view of one embodiment of the intraoral mandibular advancement device of the instant invention for attachment to six frontal teeth of the user.

As shown in FIGS. 2 and 3, at the anterior end of main body 2 is retention arc 4 which is customized to fit a plurality of the user's anterior maxillary teeth for retention of the device in the user's mouth when worn during the user's sleep state. Retention arc 4 forms a trough 5 which, in this embodiment, conforms with the user's anterior maxillary teeth for positioning (and in FIGS. 7-12 serves to retain the device, as discussed further herein below). Trough 5 formed by retention arc 4 is, in the embodiment shown in FIGS. 2-6, less than 1.0 mm in depth so that the incisal edges of the user's maxillary incisors 14 and 16 of the maxillary teeth 20 (FIG. 4) make contact with the device 1 for location, while the remainder of device 1 provides for retention. As shown in FIG. 4, retention arc 4 covers only the user's maxillary central incisors 14, lateral incisors 16, thus leaving the user's remaining maxillary teeth 20, including maxillary canine teeth 18, uncovered.

Distending from the central portion of main base 2 is protrusive element 6. Protrusive element 6 is customized to conform with the lingual surface of the user's anterior mandibular teeth. Protrusive element 6 engages the lingual surface of the user's mandibular central incisors 26 (and, if compromised periodontally or biomechanically, then extended laterally to distribute the forces over mandibular lateral incisors 28) so as to maintain a forward posture of the user's mandible relative to the maxilla. As the mandible moves forward, so does attached tongue 24, thus maintaining tongue 24 is a forward posture. When worn by the user protrusive element 6 (when properly sized) thus causes mandibular advancement sufficient to expand the oropharyngeal space and reduce any obstruction therein, including the tongue 24.

Extending from the lateral anterior portions of main body 2 are clasps 10 for retention of the device in the user's mouth when worn during the user's sleep state. Clasps 10 are customized to cover the dental and exterior surfaces of the user's upper left and right molars, preferably the first molars. Clasps 10 can be made of surgical or stainless steel or other materials known in the art. At the distal end of clasps 10 are clasp ends 12 which fit adjacent to the exterior of the upper teeth gingival to the height of contour so as to engage the undercut in order to help retain the device in the user's mouth when worn during the user's sleep state. Clasps 10 and clasp ends 12 may comprise other retentive shapes without deviating from the letter, spirit of the instant invention as disclosed and claimed.

Shown in FIG. 6 is a frontal view of protrusive element 6 positioned in use between the user's maxillary teeth 20 and mandibular teeth 31. Retention arc 4 encompasses the user's central maxillary incisors 14 and lateral maxillary incisors 16, while leaving the user's remaining maxillary teeth, if any, uncovered. The distal end of protrusive element 6 fits adjacent to the lingual side of the user's mandibular incisors so as to maintain a forward posture of the user's mandible relative to the maxilla while leaving the user's mandibular canine teeth 30 uncontacted.

Shown in FIGS. 7-13 is an alternative embodiment of intraoral mandibular advancement device 1 in which the device consists essentially of a retention arc 4 having a protrusive element 6. Retention arc 4 forms a trough 5 which encompasses the user's anterior maxillary teeth thereby retaining device 1 in the user's mouth during use.

As shown in FIGS. 8, 10, 12 and 13, protrusive element 6 engages the lingual surface of the user's anterior mandibular teeth 28 and 26 so as to maintain a forward posture of the user's mandible relative to the maxilla. As the mandible moves forward, so does the attached tongue 24, thus maintaining the tongue 24 in a forward posture. When worn by the user, protrusive element 6 thus causes mandibular advancement sufficient to expand the airway and reduce any obstruction therein, including the tongue 24.

Figure 8:
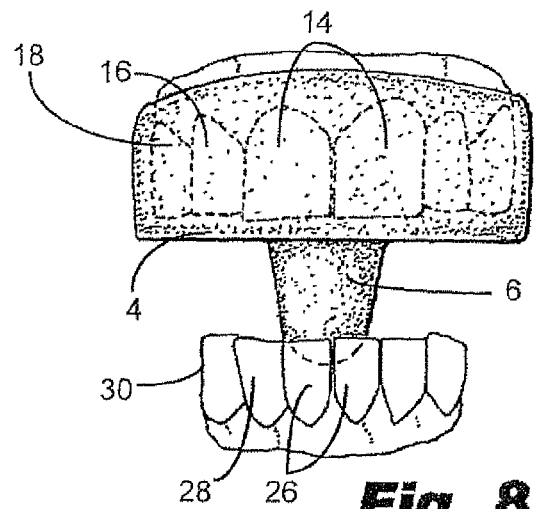
FIG. 8 is a perspective view of the embodiment of the intraoral mandibular advancement device of the instant invention, as shown in FIG. 7, in use.
Figure 9:
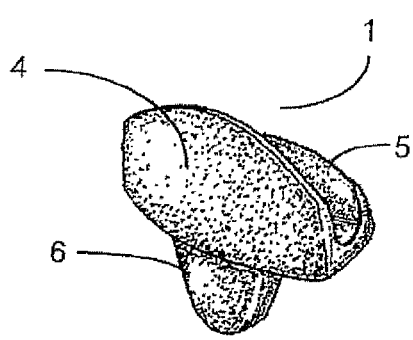
FIG. 9 is a perspective view of one embodiment of the intraoral mandibular advancement device of the instant invention for attachment to four frontal teeth of the user.
Figure 10:
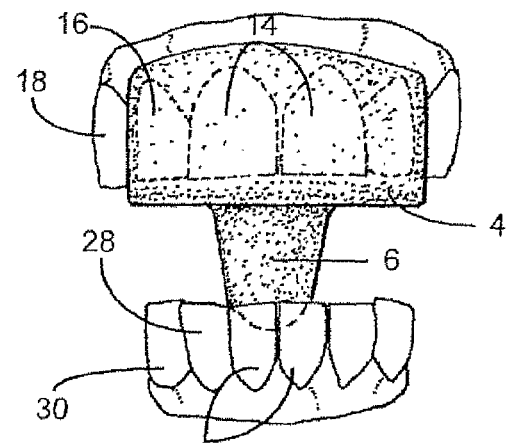
FIG. 10 is a perspective view of one embodiment of the intraoral mandibular advancement device of the instant invention, as shown in FIG. 9, in use.
Figure 11:
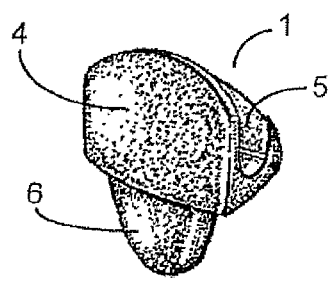
FIG. 11 is a perspective view of one embodiment of the intraoral mandibular advancement device of the instant invention for attachment to two front teeth of the user.
Figure 12:
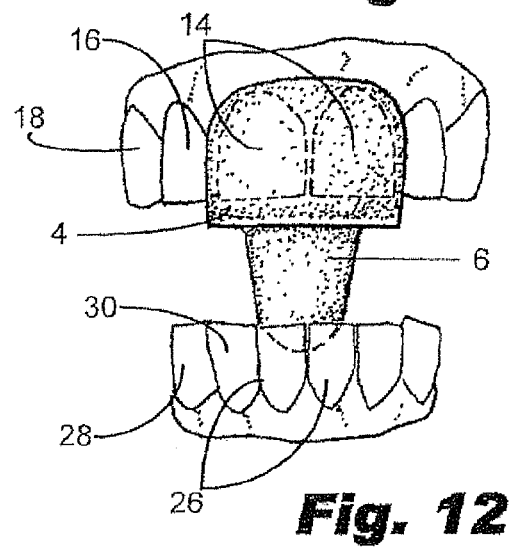
FIG. 12 is a perspective view of one embodiment of the intraoral mandibular advancement device of the instant invention, as shown in FIG. 11, is use.
Figure 13:
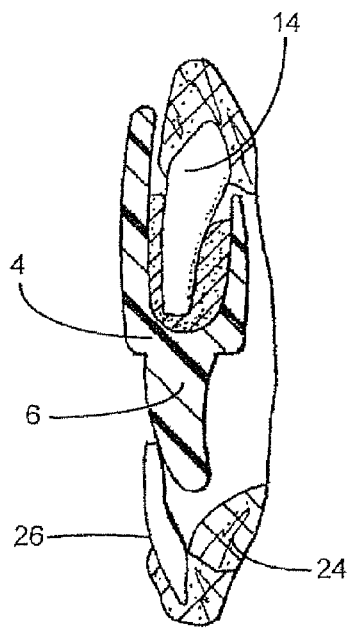
FIG. 13 is a vertical cross-sectional view of one embodiment of the intraoral mandibular advancement device of the instant invention.

As shown in FIGS. 8, 10 and 12, protrusive element 6 contacts only the lingual surface of the user's central mandibular incisors 26, thus leaving the lateral mandibular incisors 28 and mandibular canine teeth 30 uncovered.

As shown in FIG. 8, the user's central maxillary incisors 14, lateral maxillary incisors 16, and maxillary canine teeth 18 are encompassed by device 1 to provide retention in the user's mouth during use; the user's remaining maxillary teeth, if any, remain uncovered by device 1.

As shown in FIG. 10, the user's central maxillary incisors 14 and lateral maxillary incisors 16 are encompassed by device 1 to provide retention in the user's mouth during use; the user's remaining maxillary teeth, if any, including the maxillary canine teeth, remain uncovered by the device 1.

As shown in FIG. 12, the user's central maxillary incisors 14 are encompassed by device 1 to provide retention in the user's mouth during use, the user's remaining maxillary teeth, if any, including the user's lateral maxillary incisors 16 and maxillary canine teeth 18 remain uncovered by the device 1. Thus, six maxillary teeth are encompassed in FIGS. 7 and 8, four maxillary teeth in FIGS. 9 and 10, and two maxillary teeth in FIGS. 11 and 12.

Figure 14:
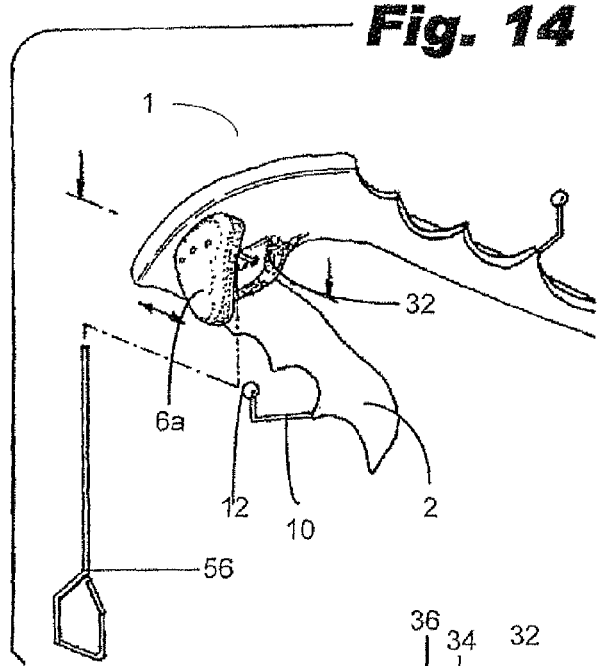
FIG. 14 is a bottom view of the preferred embodiment of the intraoral mandibular advancement device of the instant invention showing adjustability as further defined herein below.
Figure 15:
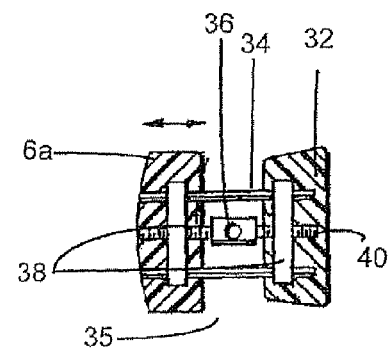
FIG. 15 is an enlarged, cross-sectional view of the adjustable mechanism of the device shown in FIG. 14.
Figure 16:
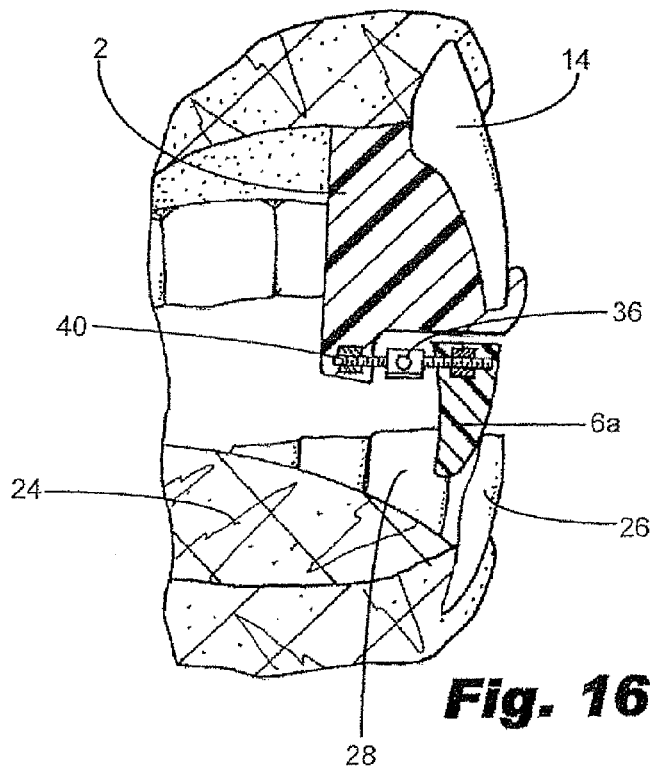
FIG. 16 is a schematic, side elevational view of the preferred embodiment of the instant invention, shown in FIG. 14, inserted in the oral region of a user.

Shown in FIGS. 14-16 is an alternative embodiment of the intraoral mandibular advancement device 1 which is essentially similar to that disclosed in FIGS. 2-5, yet contains an adjustable protrusive element 6a. Adjustable protrusive element 6a allows the user (typically via the dentist) to incrementally advance the degree of anterior protrusion for optimal placement behind the users anterior mandibular teeth. It is recognized that the smallest amount of mandibular advancement necessary to attain a patent airway should be used to maximize both efficacy and comfort, and hence compliance.

The portion of main body 2 adjacent to expansion means 35 is expansion base 32. Also running perpendicular through adjustable component plates 38 is threaded rod 40 which can be rotated clockwise or counterclockwise to increase and decrease the amount of separation between adjustable protrusive element 6a and main body 2. Adjustable protrusive element 6a is attached to main body 2 by expansion means 35. Expansion means 35 contains a plurality of adjustment component plates 38 embedded in both adjustable protrusive element 6a and expansion base 32, which is continuous with main body 2. Adjustment component plates 38 have running perpendicular therethrough a plurality of parallel guiding rods 34, thereby acting to separate adjustable protrusive element 6a from main body 2. Because main body 2 is fixed in the user's mouth, increasing the amount of space between protrusive element 6a and main body 2 acts to urge the user's mandible forward relative to the user's maxilla so as to enlarge the volume of the user's airway or otherwise reduce its collapsibility. The user (typically via the dentist) may adjust the amount of mandibular advancement by inserting adjustment key 56 into aperture 36 and rotating clockwise or counterclockwise, depending on whether the user wishes expansion or contraction of protrusive element 6a relative to main body 2, and hence advance or withdraw the user's mandible relative to the user's maxilla.

Figure 17:
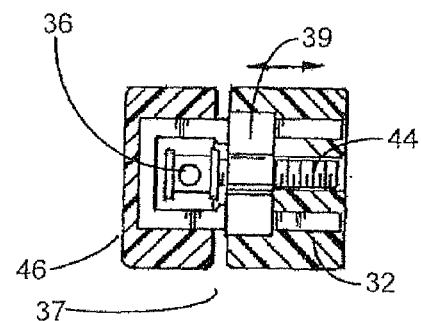
FIG. 17 is an enlarged, cross-sectional view of an alternative adjustable mechanism of the preferred embodiment of the intraoral mandibular advancement device of the instant invention.

Shown in FIG. 17 is a cross sectional view of an alternative adjustment mechanism 37 shown in a fully tightened mode. As adjustment is made via aperture 36, screw 44 is advanced via nut 39 thereby separating portion 46 from portion 42, and the entire mechanism is thus urged outwardly causing advancement, in this embodiment. Mechanism 37 can be inserted in either direction for functionality.

Figure 18:
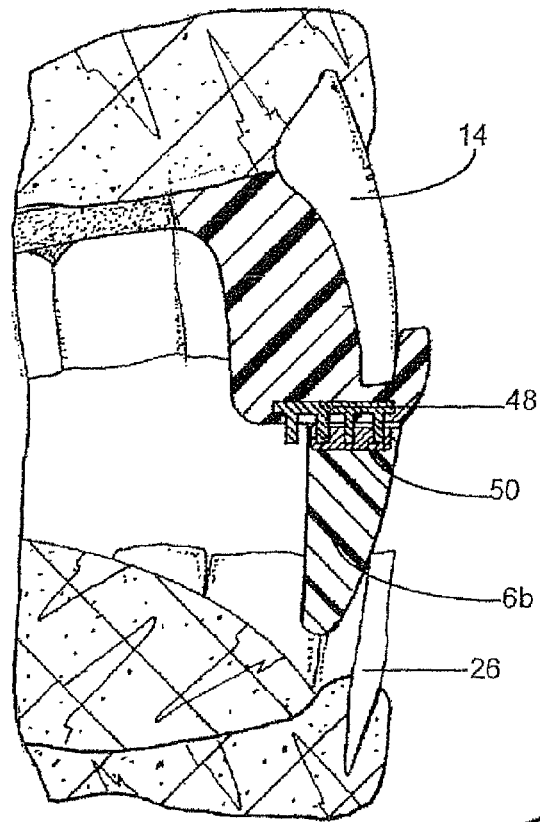
FIG. 18 is a schematic, side elevational view of yet another alternative adjustable mechanism of the preferred embodiment of the instant invention shown in the oral region of a user.

FIG. 18 is a schematic, side elevational view of one embodiment of the instant invention shown in the oral region of a typical person. In this embodiment upper adjustable snap assembly 48 engages lower adjustable snap assembly 50 such that each movement anteriorly or posteriorly causes protrusive element 6b to move accordingly. By snapping the device is thereby held in place. In this instance, about seven positions are available, although the assembly is not thereby restricted by one of ordinary skill in the art with the eye towards optimizing proper and sufficient displacement to open the airway.

Figure 19:
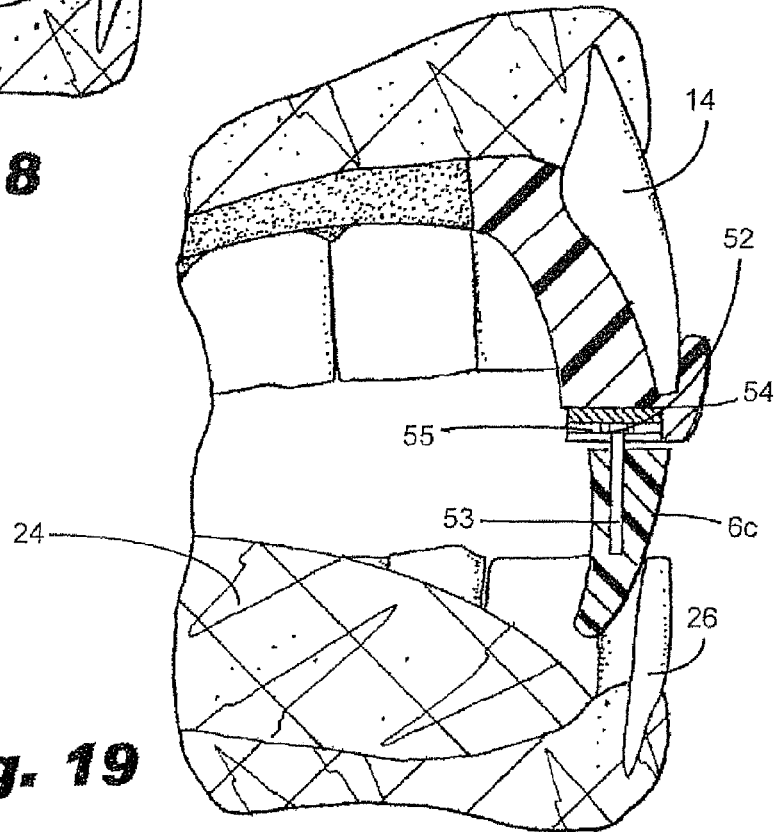
FIG. 19 is a schematic, side elevational view of yet another alternative adjustable mechanism of the preferred embodiment of the instant invention shown in the oral region of a user.

FIG. 19 is a schematic, side elevational view of one embodiment of the instant invention shown in the oral cavity of a typical person. In this embodiment, rod 53 is contained in protrusive element 6c and is threaded in the upper portion thereof to engage sliding nut 52. Sliding nut 52 travels longitudinally along track 55 and is screwable to enable rod 53 and thereby protrusive element 6c to be adjusted and fixed in a desired location.

Figure 20:
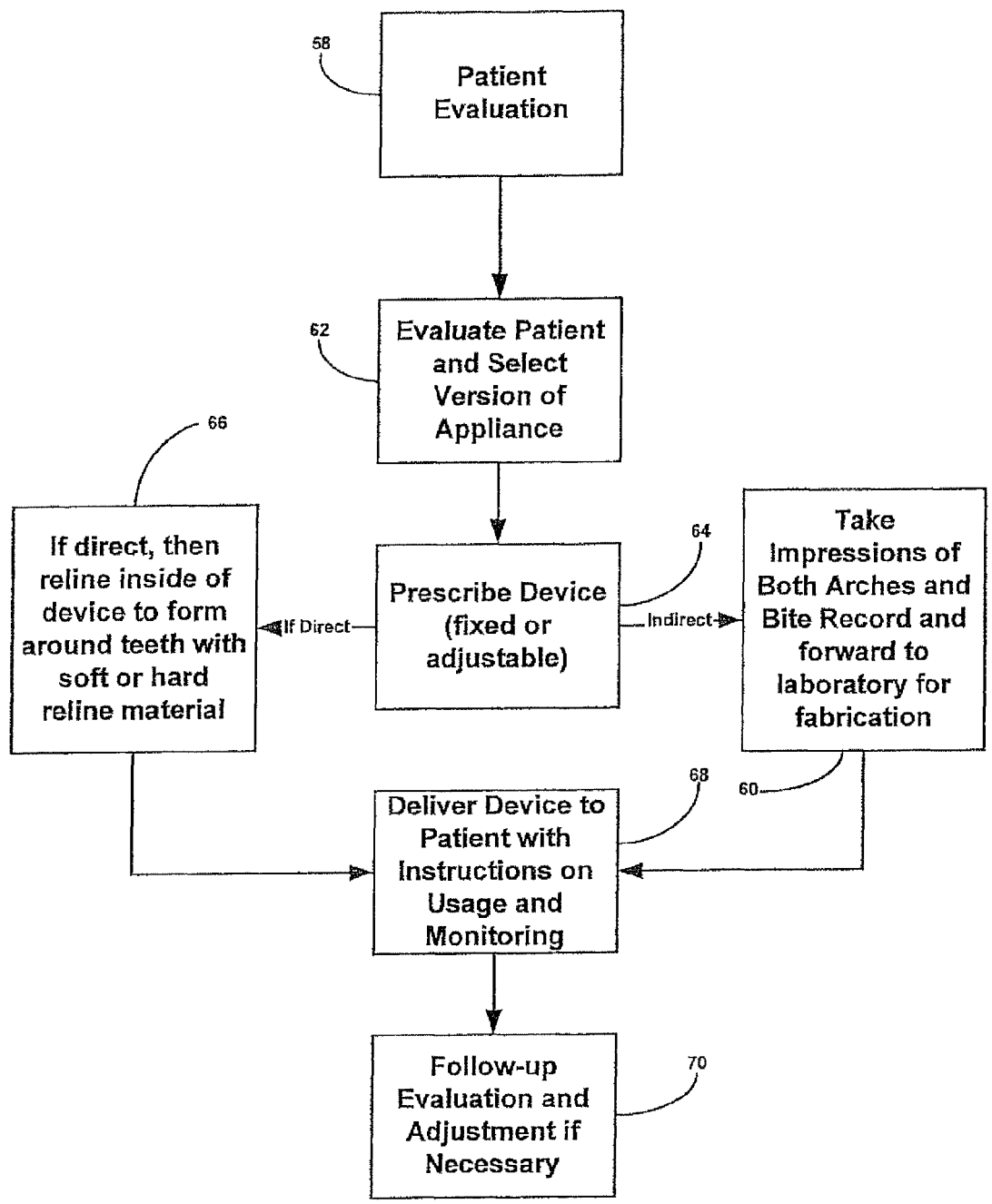
FIG. 20 is a flow chart of the underlying logic of the method and system of the preferred embodiment of the subject invention showing the sequence of events for making the same.

FIG. 20 is a flow chart of the underlying logic of the method and system of one embodiment of the subject invention showing the sequence of events for making the same. In this diagram, the method is shown wherein the patient is evaluated at step 58, and then a version of the device is selected at step 62. The selected version of the device (whether tooth-borne or palate-borne) is further determined to be delivered as either a fixed appliance or made adjustable at step 64. If an adjustable version is selected, then the mechanism for adjustment is chosen from the plurality of mechanisms shown, or their like kind. At this point, one of the alternatives is presented. If the "direct" approach is selected, then the device is ordered, received, and must be customized for the patient by relining the inside of the device to form around teeth with soft or hard reline material at step 66. If the "indirect" approach is selected, then impressions are taken at step 60, and sent to the laboratory for fabrication of the selected device. The device, upon receipt, is then delivered to the patient at step 68 with instructions on usage and monitoring. It is only through patient feedback (or that of the bed partner) that the precise dimensions can be fine tuned to ensure maximum relief from sleep disorders with minimum displacement of the mandible relative to the maxilla—the goal of the instant invention. Thus, there is follow-up and evaluation and adjustment if necessary via step 70. It should be appreciated by one of ordinary skill in the art upon reading and studying the instant invention that where such adjustment is to be made to a "fixed" or non-adjustable device, this occurs by the addition or subtraction of material from the protrusive element. Where the device provides for adjustment in any of a number of ways, then such adjustment is accomplished in that manner in accordance with the design selected.

The instant invention is shown to be effective, as demonstrated by the following studies:

Study 1. Patient of age 51 presents with loud snoring and moderate to severe apnea, theretofore treated with a CPAP device. The CPAP device is replaced with a fixed device in accordance with the subject invention creating a 4.0 mm anterior displacement of the mandible. Patient reports complete elimination of snoring while wearing the appliance for a 14 day trial.

Study 2 Patient of age 76 suffered from chronic snoring which was loud enough to awaken the patient's bed partner, theretofore treated with a number of pharmaceuticals. The pharmaceuticals were replaced with a fixed device in accordance with the subject invention creating a 4.0 mm anterior displacement of the mandible. Patient reports a significant reduction in snoring while wearing the appliance for a 14 day trial.

Study 3. Patient of age 50 suffered from snoring for many years, theretofore treated with pharmaceuticals such as Lipitor, as well as over-the-counter remedies such as vitamins and Tylenol. The pharmaceuticals and over-the-counter remedies were replaced with a fixed device in accordance with the subject invention creating a 4.0 mm anterior displacement of the mandible. Patient reports a significant reduction in snoring while wearing the appliance for a 14 day trial.

Study 4. Patient of age 55 suffered from snoring, theretofore treated with pharmaceuticals. The pharmaceuticals were replaced with a fixed device in accordance with the subject invention creating a 4.0 mm anterior displacement of the mandible. Patient reports a significant reduction in snoring while wearing the appliance for a 14 day trial.

Study 5. Patient of age 51 suffered from snoring which was loud enough to awaken people sleeping in adjacent rooms, theretofore untreated. A fixed device in accordance with the subject invention creating a 4.0 mm anterior displacement of the mandible was fitted for the patient. Patient reports a complete elimination in snoring while wearing the appliance for a 14 day trial. Likewise, it is scientifically reasonable to conclude that such patients suffered a lowering of apneatic events and therefore GERD to the extent thereby related.

FIGS. 21-26 show another embodiment of the present invention incorporating a mandibular appliance with a lingual spacer 80 to keep constant a desired degree of protrusion of the mandible at variable positions of mouth opening, irrespective of the shape or inclination of the lower teeth. In this embodiment, the assembly of maxillary components discussed above (i.e., the main body 2, protrusive element 6, and retention arc 4) can be considered to be a "maxillary appliance." In contrast to the previous embodiments, this embodiment dictates that the protrusive element 6 has a leading edge consistent with the arc of opening and closing. In particular, this embodiment also includes a mandibular appliance with a lingual spacer 80 extending posteriorly from the anterior mandibular teeth 26 to create a contact for the protrusive element 6 of the maxillary appliance, thereby maintaining a desired degree of mandibular advancement even at variable vertical positions of the mandible. The lingual spacer 80 is essentially a "mate" for the protrusive element 6. The lingual spacer 80 can have an arcuate posterior surface and be mounted to a thin polymeric shell or aligner 85 with recesses that receive at least some of the user's anterior mandibular teeth (e.g., the incisors 26, 28) as shown in FIGS. 23-24, or all of the user's lower teeth. Additionally, this thin shell helps to manage the risk of flairing or proclination of the lower teeth as a result of forces from the protrusive element 6. For example, the polymeric shell aligner 85 can be similar to those marketed by Align Technologies under the Invisalign trademark.

A major problem exists in shaping the facial side of the protrusive element 6. The anterior surface of the protrusive element 6 in previous embodiments discussed above contacts and follows the contour of the lingual aspect of the mandibular incisors. However, this approach can lead to a loss of protrusion as the vertical opening increases for two reasons. First, when the patient's mouth is opened even a few millimeters when wearing the previous embodiments of the device, the incisal edges of the mandibular incisors retrude into the concavity formed by the cingulums of these teeth and hence there would be less protrusion. Secondly, this design can be insufficient in cases with proclined mandibular anterior teeth because of the resultant slope of the protrusive element 6 would also allow retrusion as the lower jaw opens. It is this dependence on the random inclination of the lower anterior teeth, coupled with the anatomy of the lingual surfaces of the lower anterior teeth (cingulums), that has led the present inventor to develop the embodiment of the device shown in FIGS. 21-26.

Figure 21:
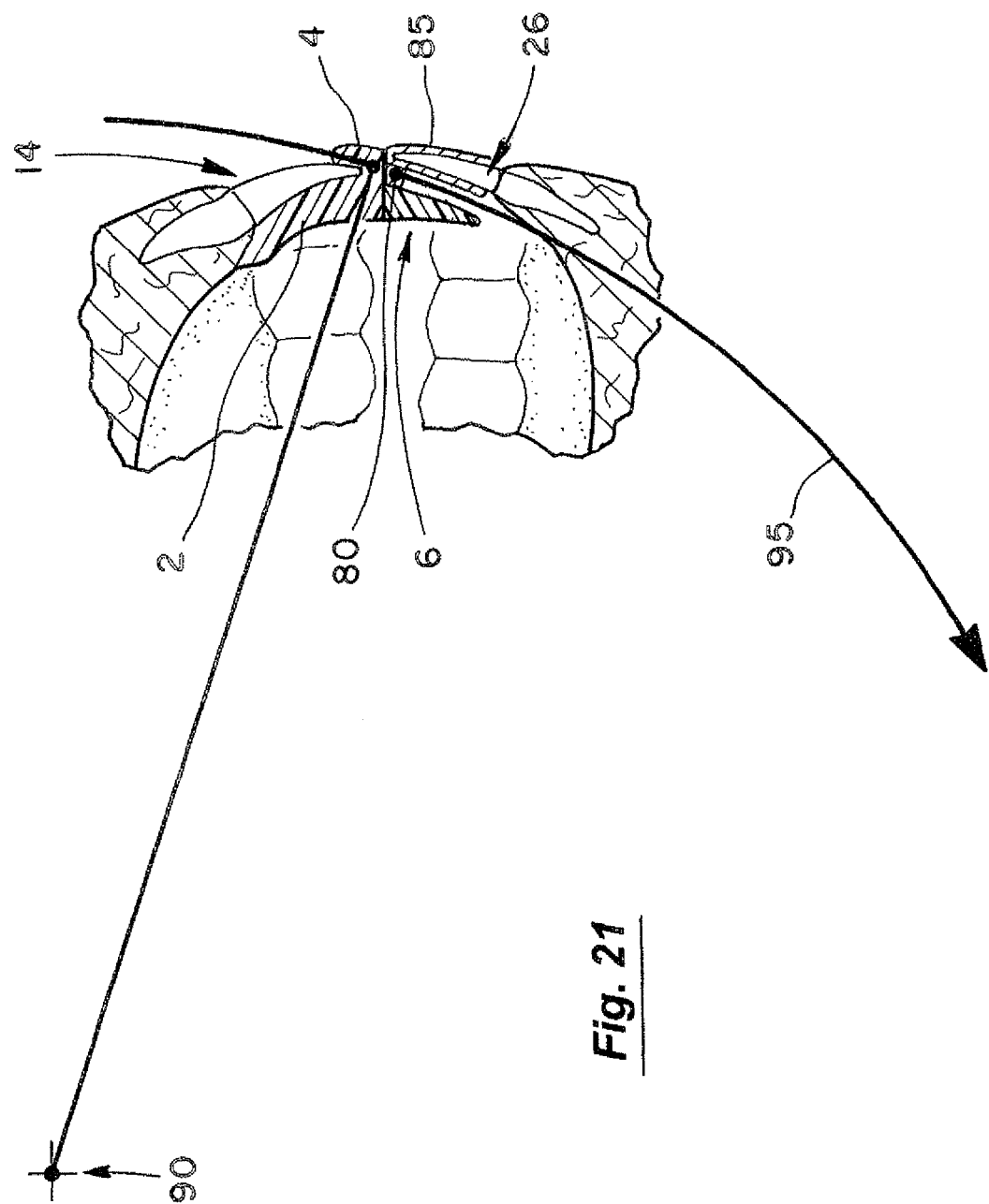
FIG. 21 is a vertical cross-sectional view of embodiment of the present invention that includes a mandibular appliance having a lingual spacer 80.

Ideally in this new embodiment, the anterior (or facial) aspect of the protrusive element 6 should be parallel to the "arc of opening and closing" 95, as illustrated in FIG. 21. This arc 95 has been well documented in the literature. Bonwill's Equilateral Triangle (1887), Monson's Spherical Theory (1932), and Weinberg's studies (1963) have described an arc that is defined by the motion of the incisal edges of the lower incisors 26 as they rotate around the condylar hinge axis 90 of the mandible. This arc 95, as determined by a radius from the condylar hinge axis 90, has also been well illustrated in Posselt's envelope of mandibular movement. At any amount of protrusion, this arc 95 will typically be defined by a radius of about 100 mm or 4 inches (i.e., the distance from the hinge axis of the condyles to the lower incisors is generally constant irrespective of the protrusiveness).

The starting position of the lower incisors 26 is between 32 mm and 50 mm below the horizontal plane 92 of the condylar hinge axis 90 of the mandible 90. This geometric relationship will be fairly consistent because although the mandibular incisors will be initially about 4 mm lower than this, it should be noted that the mandibular condyles will also drop about the same amount vertically as they move down and forward along the posterior eminence of the maxilla (average inclination of 30 degrees-reference Gysi) during this protrusion. It is generally accepted to begin with a treatment position of about 60%-70% of the range of motion anterior to the most retruded position. Considering that the average range of motion is about 10-12 mm, therapy should be initiated in a position about 7 mm protruded from the maximum intercuspal position (MIP).

It should be noted that this embodiment avoids the use of hardware that connects the two dental arches to enhance comfort and increase patient compliance, which remains one of the most significant challenges for the OSA patient. Although patients exhibit a range of vertical positions during sleep, few open more than 15 mm, which would be necessary to disengage the protrusive element 6 because it is about 10 mm long and sits on the 2 mm thick anterior stop platform on the occlusal surface of the maxillary appliance, and this must be added to 2-3 mm of normal overbite.

The mandibular appliance can be fabricated by thermoforming a plastic aligner 85 from canine to canine, or extended posteriorly to cover all the lower teeth. The lingual spacer 80 can be built from the lingual surface of mandibular appliance (approximately 2 mm in vertical thickness) and extends horizontally in the lingual direction sufficiently to meet the leading edge of the protrusive element 6 so that it prevents the protrusive element 6 from engaging any other part of the lower teeth. For example, the lingual spacer 80 can extend posteriorly by about 1-4 mm depending on the inclination of the lower incisors and the shape of their cingulums. This will effect a generally constant amount of protrusion irrespective of the vertical opening of the mouth. Alternatively, the lingual spacer 80 could be a separately formed component that is bonded to the lingual surface of the mandibular appliance.

The following is a summary of one possible fabrication protocol for the maxillary and mandibular appliance in this embodiment. The patient's models are initially set in MIP so that the lower incisors are about 100 mm from the hinge axis 90 and about 32 mm to 50 mm below the horizontal plane 92 of the hinge axis 90. A first line is drawn on the models in the molar region, and a second line is drawing about 7 mm forward on the upper model. The components of the maxillary appliance are then fabricated without attaching the protrusive element 6. The lower model is advanced to align with the second line on the upper model. The lingual spacer 80 is fabricated as part of the lower retainer. The protrusive element 6 is positioned so that it touches the lingual spacer 80, and the protrusive element 6 is then bonded in that position to the maxillary appliance.

Another fabrication protocol is for the dentist to make a record of an appropriate bite position and present that record to the laboratory for the purpose of orienting the upper and lower tooth models in the prescribed treatment position. In this approach, the dentist will measure the range of motion with a "George Gauge" and then set the gauge to the desired protrusion, record this relationship, and send it to the laboratory for fabrication in this position.

Figure 27:
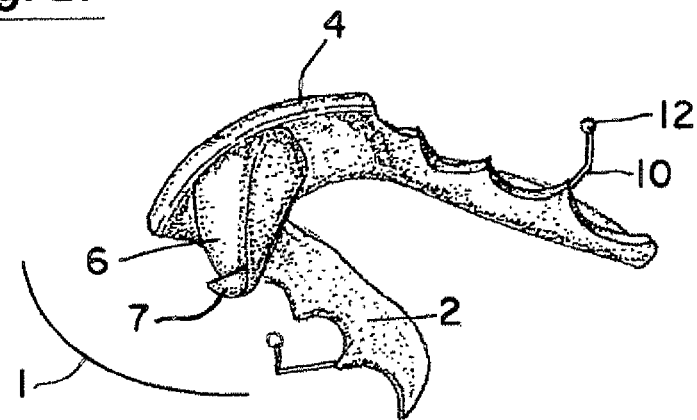
FIG. 27 is a bottom perspective view of an embodiment of the intraoral mandibular advancement device including a stop 7 on the anterior face of the protrusive element 6.
Figure 28:
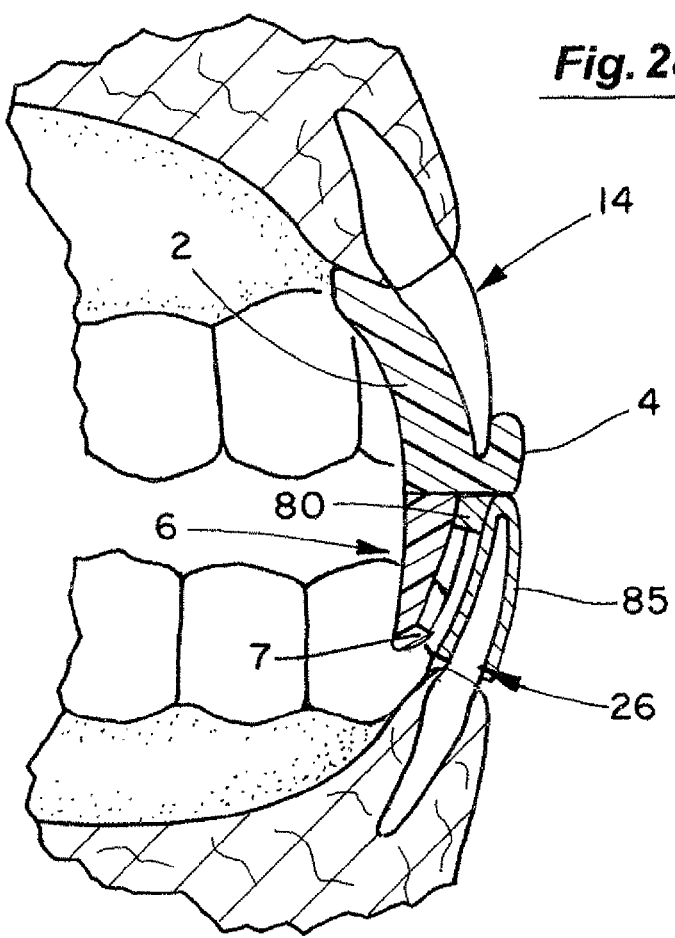
FIG. 28 is a vertical cross-sectional view of the embodiment of the device in FIG. 27 in a patient's mouth.

FIGS. 27 and 28 show another embodiment of the present invention that incorporates a small stop 7 to help prevent the possibility of uncoupling the protrusive element 6 from the lingual spacer 80 in the event of an unusually wide opening movement of the lower jaw. FIG. 27 is a bottom perspective view of this embodiment and FIG. 28 is a corresponding vertical cross-sectional view of this device in a patient's mouth. The stop 7 extends in the anterior direction (e.g., about 1-2 mm) from the lower portion anterior face of the protrusive element 6. The upper surface of the stop 7 contacts the lower surface (i.e., underside) of the lingual spacer 80 to limit the range of motion between the protrusive element 6 and the lingual spacer 80.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. An intraoral mandibular advancement device to treat problems associated with sleep disorders in a user having an obstructed oropharyngeal space comprising:
   a maxillary appliance having:
   (a) a main body for attachment to a user's maxillary teeth and having a central portion;
   (b) a protrusive element distending from the central portion of the main body and having an anterior surface with an aspect parallel to an arc defined by the motion of the incisal edges of the user's lower incisors as they rotate around the condylar hinge axis of the user's mandible; and
   (c) retention means extending from the main body for retention of the maxillary appliance to a user's maxillary anterior teeth only to prevent contact on the user's posterior teeth, thereby preventing clenching forces from being exerted on the user's posterior teeth; and
   a mandibular appliance for attachment to a user's mandibular anterior teeth to prevent contact on the user's posterior teeth having a polymeric shell with recesses to receive at least a user's anterior mandibular teeth, thereby preventing clenching forces from being exerted on the user's posterior teeth, and having a lingual spacer extending posteriorly from the anterior teeth to contact the protrusive element of the maxillary appliance, thereby causing mandibular advancement to expand the oropharyngeal space and maintain separation of the user's upper and lower posterior teeth to prevent clenching forces on the user's posterior teeth.

2. The intraoral device of claim 1 wherein the protrusive element further comprises an anterior surface and the lingual spacer further comprises a posterior edge that contacts the anterior surface of the protrusive element.

3. The intraoral device of claim 1 wherein the lingual spacer further comprises an arcuate posterior surface.

4. The intraoral device of claim 1 wherein the lingual spacer extends posteriorly about 1-4 mm.

5. The intraoral device of claim 1 wherein the protrusive element distends about 10 mm downwardly from the main body.

6. The intraoral device of claim 1 wherein the protrusive element distends between 5 and 15 mm downwardly from the main body.

7. The intraoral device of claim 1 wherein the retention means comprises a retention arc for engaging a user's maxillary incisors.

8. The intraoral device of claim 1 further comprising a stop on the lower anterior face of the protrusive element limiting the range of motion between the protrusive element and the lingual spacer.

9. An intraoral mandibular advancement device to treat problems associated with sleep disorders in a user having an obstructed oropharyngeal space comprising:
   a maxillary appliance having:
   (a) a main body for attachment to a user's maxillary teeth and having a central portion;
   (b) a protrusive element distending from the central portion of the main body and having an anterior surface with an aspect parallel to an arc defined by the motion of the incisal edges of the user's lower incisors as they rotate around the condylar hinge axis of the user's mandible; and (c) a retention arc extending from said main body for retention of the maxillary appliance to a user's maxillary incisors only to prevent contact on the user's posterior teeth, thereby preventing clenching forces from being exerted on the user's posterior teeth; and a mandibular appliance having:

(a) a polymeric shell for removable attachment to a user's mandibular anterior teeth to prevent contact on the user's posterior teeth, thereby preventing clenching forces from being exerted on the user's posterior teeth; and (b) a lingual spacer extending posteriorly from the anterior teeth and having a posterior edge for contacting the anterior surface of the protrusive element of the maxillary appliance, thereby causing mandibular advancement to expand the oropharyngeal space and maintain separation of the user's upper and lower posterior teeth to prevent clenching forces on the user's posterior teeth.

10. The intraoral device of claim 9 wherein the lingual spacer comprises an arcuate posterior surface.

11. The intraoral device of claim 9 wherein the lingual spacer extends posteriorly about 1-4 mm.

12. The intraoral device of claim 9 wherein the protrusive element distends about 10 mm downwardly from the main body.

13. The intraoral device of claim 9 wherein the protrusive element distends between 5 and 15 mm downwardly from the main body.

14. The intraoral device of claim 9 further comprising a stop on the lower anterior face of the protrusive element limiting the range of motion between the protrusive element and the lingual spacer.

* * * * *

UNITED STATES PATENT AND TRADEMARK OFFICE
CERTIFICATE OF CORRECTION

PATENT NO. : 7,730,891 B2  Page 1 of 1
APPLICATION NO. : 11/965161
DATED : June 8, 2010
INVENTOR(S) : Steven B. Lamberg It is certified that error appears in the above-identified patent and that said Letters Patent is hereby corrected as shown below:

Abstract, line 12, replace "lingual space" with --lingual spacer--.

Signed and Sealed this

Tenth Day of August, 2010

David J. Kappos
*Director of the United States Patent and Trademark Office*